United States Patent [19]
McKinzie

[11] Patent Number: 5,229,127
[45] Date of Patent: * Jul. 20, 1993

[54] RAPID MIOSIS WITH CONTROL OF INTRAOCULAR PRESSURE USING A MIXTURE OF A CETYLCHOLINE AND CARBACHOL DERIVATIVES

[76] Inventor: James W. McKinzie, 3124 Solimar Beach Dr., Ventura, Calif. 93001

[*] Notice: The portion of the term of this patent subsequent to Apr. 23, 2008 has been disclaimed.

[21] Appl. No.: 621,082

[22] Filed: Dec. 3, 1990

Related U.S. Application Data

[63] Continuation of Ser. No. 318,753, Mar. 3, 1989, Pat. No. 5,009,892.

[51] Int. Cl.$^5$ .................. A61K 9/00; A61K 31/14; A61J 1/00; B65D 39/16
[52] U.S. Cl. ......................... 424/427; 424/422; 514/912; 514/913; 215/231; 215/263; 215/265; 215/294; 215/301; 215/DIG. 3
[58] Field of Search ............... 424/422, 423, 427, 428; 514/912-915

[56] References Cited

U.S. PATENT DOCUMENTS

| | | | |
|---|---|---|---|
| 3,870,791 | 3/1975 | Haddad et al. | 424/22 |
| 4,405,627 | 9/1983 | Masi et al. | 424/263 |
| 4,459,309 | 7/1984 | Chiou | 424/300 |
| 4,490,379 | 12/1984 | Podos et al. | 424/262 |
| 4,665,094 | 5/1987 | Baldwin et al. | 514/546 |
| 4,853,224 | 8/1989 | Wong | 424/427 |
| 5,009,892 | 4/1991 | McKinzie | 424/422 |

OTHER PUBLICATIONS

Gormaz, A., *Ocular Tension After Cataract Surgery*, American Journal of Ophthalmology, 43:832, 1962.
Rich, W. J. C. C., *Intraocular Pressure and Wound Closure After Cataract Extraction*, Trans. Ophthalmol. Soc., U.K. 88:437, 1968.
Rich, W. J. C. C., *Further Studies on Early Post-Operative Ocular Hypertension Following Cataract Extraction*, Trans. Ophthalmol. Soc., U.K. 89:639, 1969.
Olivius, E., and Thornburn, W., *Intraocular Pressure After Cataract Surgey with Healon*, Am. Intraocular Implant Soc. J. 11:480, 1985.
Cherfan, G. M., Rich, W. J. and Wright, G., *Raised Intraocular Pressure and Other Problems with Sodium Hyaluronate and Cataract Surgery*, Trans. Ophthalmol. Soc., U.K., 103:277, 1983.
Obstbaum, S. A. and Galin, M. W., *The effects of Timolol on Cataract Extraction and Intraocular Pressure*, Am. J. Ophthalmol., 88:117, 1979.
Tomoda, T., Tuberville, A. W. and Wood, T. O., *Timolol and Postoperative Intraocular Pressure*, Am. Intraocul. Implant Soc.J., 10:180, 1984.
Ruiz, R. S., Wilson, C. A., Mugrove, K. H. and Prager,

(List continued on next page.)

Primary Examiner—Thurman K. Page
Assistant Examiner—E. J. Webman
Attorney, Agent, or Firm—Marvin E. Jacobs

[57] ABSTRACT

Quick miosis with 24 hour control of intraocular pressure of patients undergoing extracapsular cataract extraction surgery is achieved by applying to the eyes of the patient during surgery acetylcholine as a first miotic agent and carbachol as a second miotic agent. Acetylcholine provides quick miosis while carbachol enhances the miotic effect while providing post-surgery control of intraocular pressure. The two miotic agents can be dissolved in a common saline carrier. The two agents can be combined in a unit dosage package by disposing acetylcholine in powder form in a first compartment and a solution of carbachol in a second compartment. The combined miotic agent of the invention is especially useful when substances which raise IOP such as viscoelastic agents are used during ocular surgery and/or with sensitive patients who enter the surgery with elevated pressure such as those suffering from glaucoma.

18 Claims, 5 Drawing Sheets

OTHER PUBLICATIONS

T. C., *Management of Increased Intraocular Pressure After Cataract Extraction*, Am. J. Ophthamol., 103:487, 1987.

Beasley, H., *Miotics in Cataract Surgery*, Arch, Ophthalmol., 88:49, 1972.

Douglas, G. R., *A Comparison of Acetylcholine and Carbachol Following Cataract Extraction*, Can. J. Ophthalmol. 8:75, 1973.

Holland, R. H., Drance, S. M., & Schulzer, M., *The Effect of Intracramerol Carbachol on Intraocular Pressure After Cataract Extraction*, Am. J. Ophthalmol, 104:225, 1987.

Hollands, R. H., Drance, S. M., & Schulzer, M., *The Effect of Acetylcholine on Early Postoperative Intraocular Pressure*, Am. J. Ophthalmol., 103:749, 1987.

Hayreh, S. S., *Anterior Ischemic Optic Neuropathy, IV, Occurrence After Cataract Extraction*, Arch. Ophthalmol., 98:1410, 1980.

Yee; R. W. and Edelhauser, H. F., *Comparison of Intraocular Acetylcholine and Carbachol*, J. Cataract Refract Surg., 12:18, 1986.

McKinzie, J. W. & Boggs, Jr., M. B., *Comparison of Postoperative Intraocular Pressures After Use of Miochol and Miostat*, J. Cataract Refract. Surg. 15:185, 1989.

Linn, D., Zimmerman, T., Nardin, G., Yung, R., Berberich, S., DuBiner, H., Fuque, M., *Effect of Intracameral Carbachol on Intraocular Pressure After Cataract Extraction*, Am. J. Ophthalmol., 107:133-136, Feb. 1989.

Ruiz, R., Rhem, M., & Prager, T., *Effects of Carbachol and Acetylcholine on Intraocular Pressure After Cataract Extraction*, Am. J. Opthalmol., 107:7-10, Jan. 1989.

A. Pilz, J. Pilz & W.-D. Ulrich, *Interference of Directly Acting Cholinergics on the Isolated Sphincter Pupillae and Ciliary Muscle*, Folia Opthal.4(1979), 34-45.

Wood, T., *Effect of Carbachol on Postoperative Intraocular Pressure*, J. Cataract Refract. Surg.-vol. 14, Nov. 1988.

McDonald, T., Beasley, C., Borgmann, A., & Roberts, D., *Intraocular Administration of Carbamylcholine Chloride*, Annals of Ophthalmol., Oct. -Nov. 1969.

O'Brien, C. S., Swan, K. C., *Carbaminoylcholine Chloride in the Treatment of Glaucoma Simplex*, Dept. of Ophthalmol., State University of Iowa, College of Medicine.

RAPID MIOSIS WITH CONTROL OF INTRAOCULAR PRESSURE USING A MIXTURE OF A CETYLCHOLINE AND CARBACHOL DERIVATIVES

CROSS-REFERENCE TO RELATED APPLICATION

This application is a continuation of Ser. No. 318,753 filed Mar. 3, 1989 issued as U.S. Pat. No. 5,009,892.

TECHNICAL FIELD

This invention relates to a miotic agent useful in postoperative cataract and intraocular lens surgery and, more particularly, to a combination of miotic agents that provides quick miosis with control of intraocular pressure 24 hours after surgery.

BACKGROUND OF THE INVENTION

Miotic agents are frequently used by ophthalmologic surgeons during intraocular surgery. The anterior chamber is irrigated with a miotic agent after delivery of the lens in cataract surgery as well as in penetrating keratoplasty, iridectomy and other anterior segment surgery. Prompt miosis is necessary to ensure that a round pupil is obtained after cataract surgery. If any of the iris of the eye is caught in the incision or if a capsular tag is caught in the incision, the pupil will be distorted on the following day. It is easy to miss a capsular tag in the incision since the tag is clear and transparent unless one uses a miotic agent. The other advantages obtained by the use of miotics are the facilitation of post-placed corneal scleral sutures, anterior chamber lens insertion and a decrease in post-operative peripheral anterior synechias. Many surgeons feel that miotic agents help in centering and positioning the intraocular lens implant.

Elevated intraocular pressure (IOP) can interfere with normal functioning and may result in irreversible loss of visual function. Viscoelastic agents such as Healon are often used during lens implantation which can cause elevated IOP with pressure spiking.

With the advent of modern surgical techniques and the trend to "in the bag" placement of posterior chamber intraocular lens' (IOL), more and more viscoelastic substances are being used. Increasingly, cataract surgery is being done on an out-patient basis, and the patient returns to the physician's office the following day. Slit lamps and applanation tonometry are handy, and consequently most surgeons are examining their post-operative patients even better than when they were hospitalized. This has improved patient care and, on the other hand, has perhaps resulted in increased awareness of the IOP 20-24 hours after cataract surgery.

Pressure studies have shown that the IOP in the first 24 hours after cataract surgery may be very important. Damage by raising IOP is possible to the optic nerve, the vascular supply within the eye, and the corneal endothelium (15)(7). Consequently, every effort should be made to control the IOP from the very onset of the post-operative period.

Acetylcholine (Miochol) is the most popular miotic agent utilized by ophthalmologic surgeons. Miochol provides quick miosis (within minutes). However, it provides very poor control of IOP after several hours, even when pressure control agents such as acetazolamide (Diamox) are utilized. Carbachol (Miostat) does not provide as quick a miosis and is not as widely used. A miotic agent providing quick miosis with control of intraocular pressure 24 hours after surgery is needed.

DESCRIPTION OF THE PRIOR ART

Gormaz (3), in 1962, first reported increases in IOP in the immediate period after cataract extractions. Rich (4) (5) in 1968 and 1969 found a significant rise in IOP was characteristic after cataract surgery. He also showed that α-chymotrypsin was not required to produce this increase. Sodium hyaluronate (Healon) has been implicated as causing a rise in IOP. Olivius and Thornburn (6) have shown that sodium hyaluronate induced increased IOP, and is partially reversible by removal or dilution of the viscoelastic material by irrigation (7).

Several drugs have been used to counteract the increase in IOP associated with cataract surgery. Rich (3) in 1969 demonstrated a lowering of IOP 24 hours after surgery with the use of acetazolamide (Diamox) in high doses during the 24 hours following cataract surgery. However, acetazolamide has some undesirable side effects in some patients. Although Timolol effectively lowered IOP after ICCE (intracapsular cataract extraction) (8), it was found to have no effect in acute post-operative pressure evaluations following ECCE with IOL and the use of sodium hyaluronate (9). Recently, a simple administration of pilocarpine gel was found to be effective in reducing IOP for the first 24 hours after ECCE with IOL (10). However, patients frequently complained of brow ache the next day. This same group, however, felt that there was a trend in lowering IOP post-operatively using Timolol.

Miotic agents came into use in about 1970, shortly after the onset of ECCE. In 1972, Beasley (11) found that miosis was rapid with both acetylcholine 1% and carbachol 0.01%. With carbachol, miosis extended into the first post-operative day, unlike acetylcholine, where the miotic effect is gone within a very short time. However, Hollands, Drance and Schulzer (13), showed that acetylcholine 1% has a more rapid onset of miosis than does carbachol 0.01%. Hollands, Drance and Schulzer (14) showed that acetylcholine 1%, administered intracamerally during cataract surgery, significantly reduced the IOP at 3 and 6 hours post-operatively but had no effect beyond this time. On the other hand, this same group of investigators showed that carbachol 0.01% was highly effective in reducing IOP for at least 24 hours post-operatively, and in reducing the number of patients developing IOP greater than 30 mm Hg.

List of Cited References

1. U.S. Pat. No. 4,459,309.
2. U.S. Pat. No. 4,665,094.
3. Gormaz, A., Ocular Tension After Cataract Surgery, American Journal of Ophthalmology, 43:832, 1962.
4. Rich, W. J. C. C., Intraocular Pressures and Wound Closure After Cataract Extraction. Trans. Ophthalmol. Soc., U. K. 88:437, 1968.
5. Rich, W. J. C. C., Further Studies on Early postoperative Ocular Hypertension Following Cataract Extraction. Trans. Ophthalmol. Soc., U. K. 89:639, 1969.
6. Olivius, E. and Thornburn, W., Intraocular Pressure After Surgery with Healon. Am. Intraocular Implant Soc. J. 11:480, 1985.
7. Cherfan, G. M., Rich, W. J. and Wright, G., Raised Intraocular Pressure and Other Problems with Sodium Hyaluronate and Cataract Surgery. Trans. Ophthalmol. Soc., U. K. 103:277, 1983.

8. Obstbaum, S. A. and Galin, M. A., The Effects of Timolol on Cataract Extraction and Intraocular Pressure. Am. J. Ophthalmol. 88:1017, 1979.

9. Tomoda, T., Tuberville, A. W. and Ward, T. O., Timolol and Postoperative Intraocular Pressure. Am. Intraocul. Implant Soc. J., 10:180, 1984.

10. Ruiz, R. S., Wilson, C. A., Musgrove, K. H. and Prager, T. C., Management of Increased Intraocular Pressure After Cataract Extraction. Am. J. Ophthalmol., 103:487, 1987.

11. Beasely, H., Miotics in Cataract Surgery, Arch. Ophthalmol., 88:49, 1972.

12. Douglas, G. R., A Comparison of Acetylcholine and Carbachol Following Cataract Extraction. Can. J. Ophthalmol., 8:75, 1973.

13. Hollands, R. H., Drance, S. M. and Schulzer, M., The Effect of Intracamerol Carbachol on Intraocular Pressure After Cataract Extraction. Am. J. Ophthalmol., 104:225, 1987.

14. Hollands, R. H., Drance, S. M. and Schulzer, M., The Effect of Acetylcholine on Early Postoperative Intraocular Pressure, Am. J. Ophthalmol., 103:749, 1987.

15. Hayrch, S. S., Anterior Ischemic Optic Neuropathy, IV, Occurrence After Cataract Extraction, Arch. Ophthalmol., 98:1410, 1980.

STATEMENT OF THE INVENTION

An improved miotic agent is provided in accordance with this invention that provides rapid miosis with 24 hours control of intraocular pressure. The miotic agent of the invention reduces or eliminates the need for IOP control agents such as Diamox and reduces IOP after use of viscoelastic agents such as Healon.

The miotic agent of the invention resides in the combined use of an acetylcholine type of agent with a carbachol type of agent. The combination provides fast onset of miosis, a prolonged miotic effect, and long-term control of IOP for 24 hours. The IOP is maintained at or below 25 mm Hg with very few, if any, pressure spikes in the 24 hour, post-operative period.

The miotic agent of the invention is convenient to use. The agent is safe and effective since it is a combination of two agents approved for use in the same procedure. The miotic agent of the invention will find general use in intraocular surgery and is especially useful in the class of patients who enter the procedure with elevated intraocular pressure, such as glaucoma patients. It will also prove very useful in procedures in which Healon is used to aid in the insertion of an intraocular lens.

The acetylcholine and carbachol materials can be used sequentially or simultaneously. Another aspect of the invention resides in packaging the two agents in a common container having two separate compartments. The agents are combined and dissolved in a common carrier immediately before use.

These and many other features and attendant advantages of the invention will become apparent as the invention becomes better understood by reference to the following detailed description when considered in conjunction with the accompanying drawings.

BRIEF DESCRIPTION OF THE DRAWINGS

FIG. 1a is an enlarged view of a package containing the component of the miotic agent of the invention;

FIG. 1b is a view taken along line 1b—1b of FIG. 1a;

FIG. 1c is a view similar to FIG. 1b but showing unit dosage and aqueous solution mixed and ready to be withdrawn by a hypodermic needle;

DETAILED DESCRIPTION OF THE INVENTION

The first active agent in the miotic composition of the where R and $R^1$ and lower alkyl groups containing 1 to 5 carbon atoms and $X^-$ is an anion such as halo.

The preferred member of this group is acetylcholine where R and $R^1$ are all methyl and $X^-$ is chloro. Acetylcholine is a parasympathemetic agent. It is utilized in concentrations from 0.1 to 5% usually at 1% by weight. Acetylcholine is unstable so it is provided in dry powder form and is mixed with physiologically inert, liquid carrier before use. The dry material can be mixed with an inert lyophilizing material such as mannitol in ratios of 1/1 to 10/1, usually 3/1 by weight. The reconstituted aqueous solution contains 1% acetylcholine and 3% mannitol by weight. The usual doses for administration is about 2 ml.

The second active material in the miotic composition is a compound of the formula:

where $R^2$ is a low alkyl group of 1–5 carbon atoms, n is an integer from 0–3 and X is an anion such as halo. The preferred material carbachol, is a compound in which n is 0, $R^2$ are all methyl and X is chloro. Carbachol is provided as a sterile aqueous salt solution in a concentration from 0.001 to 1.0 percent by weight, usually at about 0.01% by weight. The isotonic salt carrier includes the following inactive salts:

| Salt | % by Weight |
| --- | --- |
| NaCl | 0.64 |
| KCl | 0.075 |
| CaCl$_2$.H$_2$O | 0.048 |
| MgCl$_2$.6H$_2$O | 0.03 |
| Sodium acetate.3H$_2$O | 0.39 |
| Sodium citrate.2H$_2$O | 0.17 |

The pH is adjusted to neutral with sodium hydroxide or hydrochloric acid as needed.

Figures 1A, 1B, 1C:
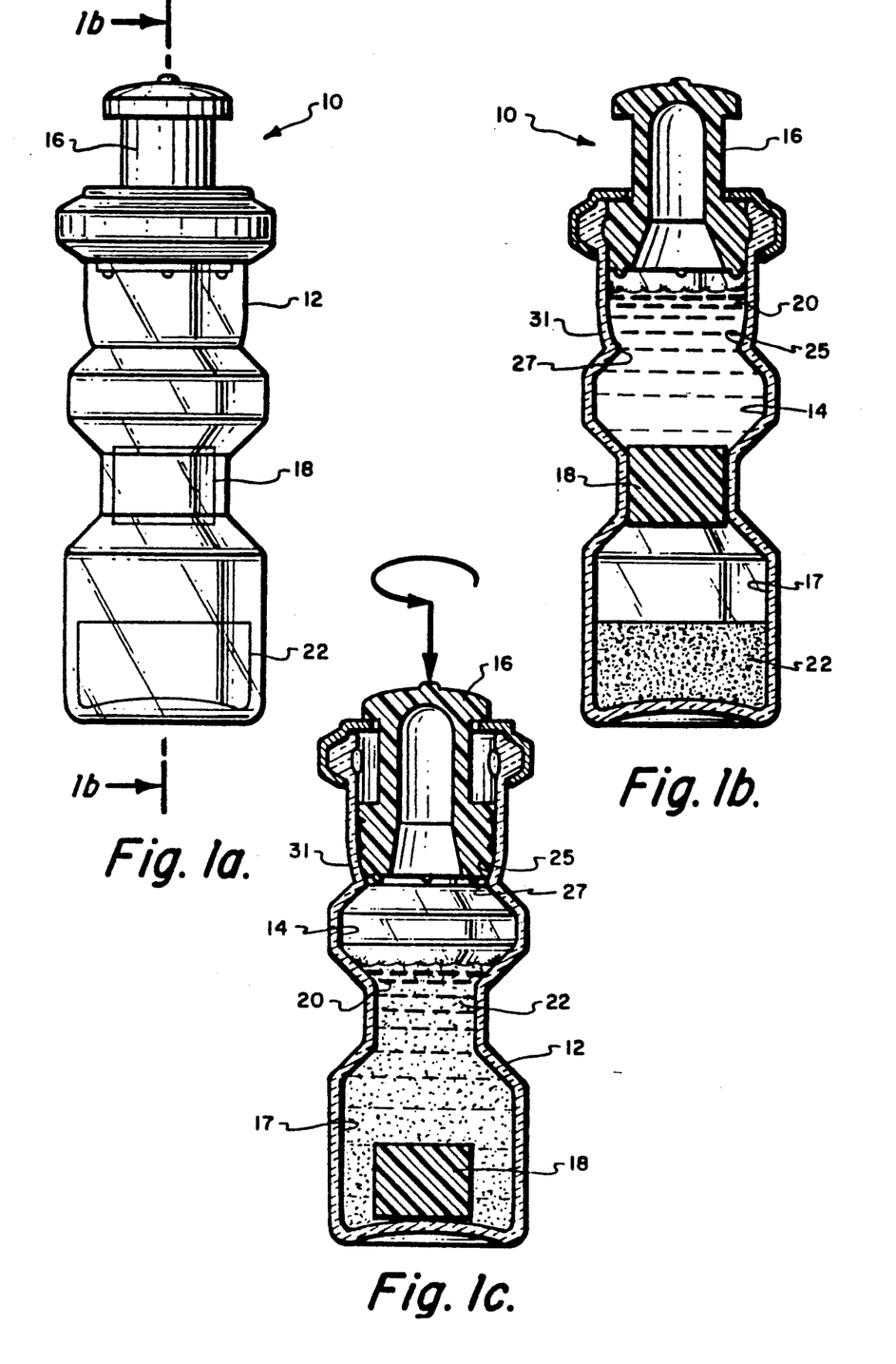

Referring now to FIG. 1, the two agents can be provided in a two compartment package 10. The package is in the form of a uni-vial 12 having a first compartment 17 sealed by a first elastomer plug 18 and a second compartment 14 sealed by a second elastomer plunger-stopper 16. The first compartment 17 contains a unit dosage or charge 22 of the first agent such as acetylcholine and the lyophilizing agent such as mannitol and the second compartment 14 contains an aqueous solution 20 of the second agent in a solution of salt in isotonic proportions and concentrations. The plunger-stopper 16 is pressed downwardly which forces the plug 18 into the lower compartment. The plunger-stopper 16 comes to rest on the shoulder 25 formed along the rim 27 of the annular section 31 of the uni-vial 12. The solution 20 falls into the first compartment 17 and dissolves the dry charge 22. In use, a hypodermic needle, not shown, is inserted through the plunger-stopper 16 into a second compartment 14 to withdraw the solution. After the dry mixture of compounds is dissolved, the combined miotic agent is withdrawn into the syringe and is ready for use.

Studies were conducted using Miochol (acetylcholine) and Miostat sequentially, and combined separately during intraocular surgical procedures.

The miotic agent of the invention can be used as follows. After extraction of a cataract, the capsule is retained. It has an anterior flap. To facilitate insertion of the lens, the capsule is inflated and Healon is applied. After insertion of the lens in the capsule, the Miochol agent is injected. As the pupil is constricting, closure of the wound takes place. The viscoelastic agent is removed from the capsule coating by aspiration with saline. The Miostat solution is then added to the anterior chamber. As the last stitching of the incision is completed, the iris is examined for roundness and for inclusion of iris or capsular tags in the incision.

When the combination of acetylcholine and carbachol is utilized in a common carrier, a portion of the combination solution is added after lens insertion and closure of the wound takes place. The viscoelastic agent is aspirated from the anterior chamber and the combination miotic agent is added again as the stitching of the wound is completed.

The following studies provide indications of the ability of the combination miotic agent of the invention to provide long-term IOP control without the use of Diamox and excellent control of glaucoma patients undergoing ECCE.

The average intraocular dose of Miochol is 0.5 to 2 ml of the 1% solution and of the carbachol during surgery is 0.5 to 2 ml of a 0.01% solution.

The intraocular pressure was measured with the Goldman applanation tonometer the day before surgery during the pre-operative visit. The second intraocular pressure measurement was taken 20-24 hours after surgery at the first post-operative visit.

SURGICAL TECHNIQUE

1. Standard ECCE with intraocular lens implantation (either PMMA (Polymethylmethacrylate) with Prolene loops, or all PMMA) was performed. All phakoemulsification with intraocular lens implantation patients were excluded. All known glaucoma patients were also excluded from this part of the study.

2. Methods and procedures: (a) Honan cuff 15-30 minutes pre-operatively, (b) approximately 11 mm incision, (c) manual extracapsular cataract extraction (pressure below, counter-pressure above), (d) Healon (sodium hyaluronate) was used in all cases, (e) machine cortical irrigation and aspiration containing epinephrine with either Site unit or Series 10,000 Coopervision unit, (f) "in the bag" placement of the posterior chamber intraocular lens, (g) machine irrigation and aspiration of Healon, (h) Miotic agent instilled into the anterior chamber and the chamber was aspirated to remove the Healon, (i) closure with interrupted 10-0 nylon sutures.

Injectable medication used at surgery were Garamycin (¼ to 1 cc), and Celestone (¼ to 1 cc).

3. Topical medications used upon completion of surgery were Tobrex, Maxidex, and Betoptic, Celestone, Maxidex and Betoptic are underlined because they are known to affect intraocular pressure.

ECCE surgery has been conducted utilizing acetylcholine and carbachol sequentially and combined on two sets of patients. All surgeries were successful with quick miosis followed by rapid lowering of IOP and low IOP after 24 hours.

Figure 8:
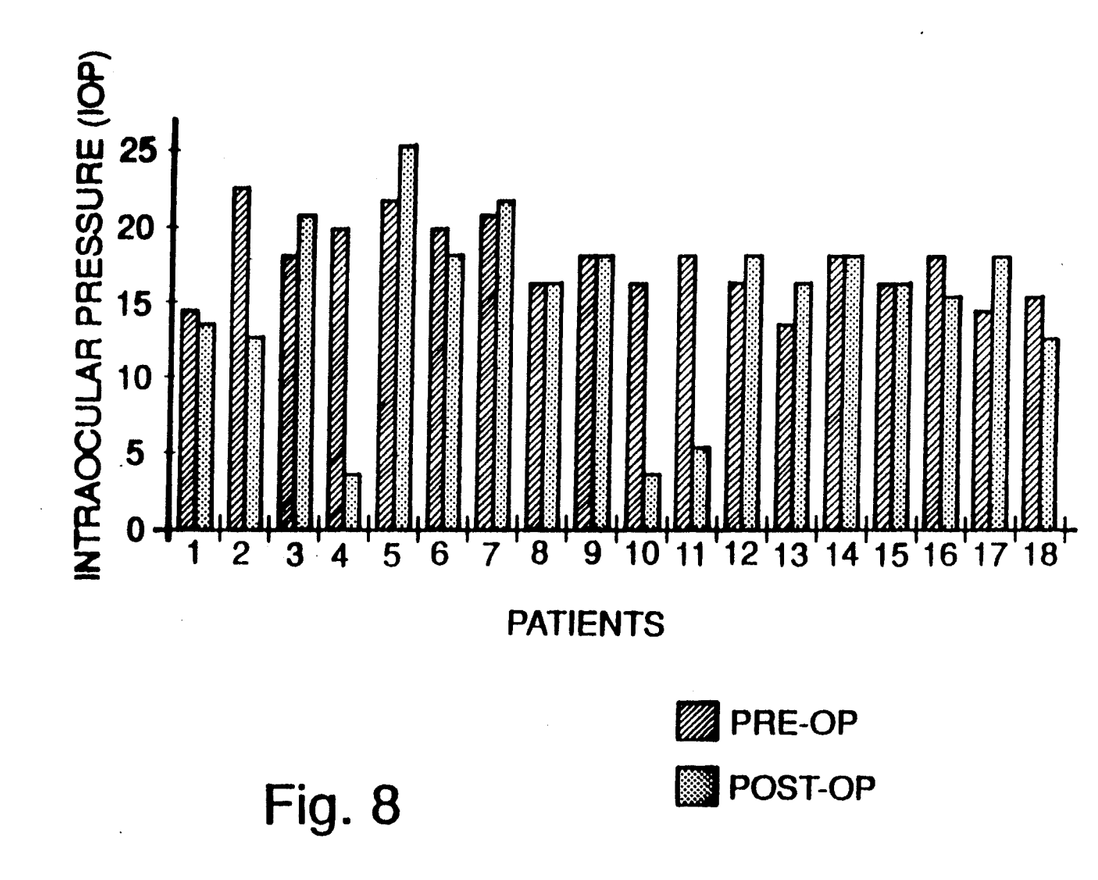
FIG. 8 is a series of bar graphs illustrating the pre- and post-operative IOP in 18 patients administered the combined miotic agent of the invention.

The following table and FIG. 8 show the IOP of 9 patients administered the two miotic agents sequentially. Quick miosis was observed. The Post-Op IOP (24 hours after surgery) was the same or lower than the Pre-Op pressure.

TABLE 1

| Patient | Pre-Op | Post-Op | Delta IOP |
| --- | --- | --- | --- |
| 1 | 15 | 15 | 0 |
| 2 | 15 | 16 | 1 |
| 3 | 12 | 7 | −5 |
| 4 | 19 | 20 | 1 |
| 5 | 18 | 13 | −5 |
| 6 | 21 | 16 | −5 |
| 7 | 16 | 10 | −6 |
| 8 | 19 | 16 | −3 |
| 9 | 18 | 16 | −2 |

The combined miotic agent of the invention was administered to 18 additional subjects. Measurements of IOP were taken on the operated eye (OP) and the fellow (FEL) eye before the operation at surgery (PRE) and 24 hours after the operation (POST). The pupil size was measured at surgery (AT) and 24 hours after surgery (POST). The following Table shows the measurements, the differences (DELTA) and the maximum, minimum and averages of the measurements.

TABLE 2

| Patient | Pre-Op | Pre-Fel | Post-Op | Post-Fel | Pupil AT | Pupil POST | Delta OP | Delta FEL |
| --- | --- | --- | --- | --- | --- | --- | --- | --- |
| 1 | 14 | 14 | 13 | 11 | 4.5 | 2 | −1 | −3 |

TABLE 2-continued

| Patient | Pre-Op | Pre-Fel | Post-Op | Post-Fel | Pupil AT | Pupil POST | Delta OP | Delta FEL |
|---|---|---|---|---|---|---|---|---|
| 2 | 22 | 23 | 12 | 26 | 4 | 4 | −10 | 3 |
| 3 | 18 | 18 | 20 | 15 | 5 | 1.5 | 2 | −3 |
| 4 | 19 | 19 | 4 | 15 | 4 | 2.5 | −15 | −4 |
| 5 | 21 | 18 | 25 | 18 | 4 | 1.5 | 4 | 0 |
| 6 | 19 | 18 | 18 | 18 | 3 | 2 | −1 | 0 |
| 7 | 20 | 20 | 21 | 17 | 3 | 2 | 1 | −3 |
| 8 | 16 | 17 | 16 | 14 | 3.5 | 2 | 0 | −3 |
| 9 | 18 | 17 | 18 | 12 | 2.5 | 2.5 | 0 | −5 |
| 10 | 16 | 16 | 4 | 16 | 4 | 2 | −12 | 0 |
| 11 | 18 | 21 | 5 | 20 | 4 | 2 | −13 | −1 |
| 12 | 16 | 16 | 18 | 18 | 4 | 2 | 2 | 2 |
| 13 | 13 | 14 | 16 | 16 | 6 | 3 | 3 | 2 |
| 14 | 18 | 20 | 18 | 26 | 3.5 | 2 | 0 | 6 |
| 15 | 16 | 16 | 16 | 15 | 4 | 2.5 | 0 | −1 |
| 16 | 18 | 19 | 15 | 18 | 3 | 2 | −3 | −1 |
| 17 | 14 | 15 | 18 | 18 | 3.5 | 2 | 4 | 3 |
| 18 | 15 | 15 | 12 | 10 | 3 | 2 | −3 | −5 |
| Max. | 22 | 23 | 25 | 26 | 6 | 4 | 4 | 6 |
| Min. | 13 | 14 | 4 | 10 | 2.5 | 1.5 | −15 | −5 |
| Ave. | 17.278 | 17.5556 | 14.944 | 16.8333 | 3.81 | 2.194 | −2.333 | −0.72222 |
| Std. | 2.4688 | 2.47867 | 5.8054 | 4.25994 | 0.82 | 0.572 | 5.9902 | 3.044871 |

The Post-Op IOP is lower than the Pre-Op IOP showing good control. The pupil is still constricted 24 hours later.

A retrospective, clinical study was conducted on pre-operative and post-operative intraocular pressures of patients administered Acetylcholine or Carbachol while undergoing extracapsular, cataract extraction with intraocular lens implantation. The surgery was performed in a similar fashion by one surgeon (the author). Intraocular pressure was measured with the Goldman applanation tonometer the day before surgery during the pre-operative visit. The second intraocular pressure measurement was taken by Goldman applanation tonometer 20–24 hours following surgery at the first post-operative visit.

Figure 2:
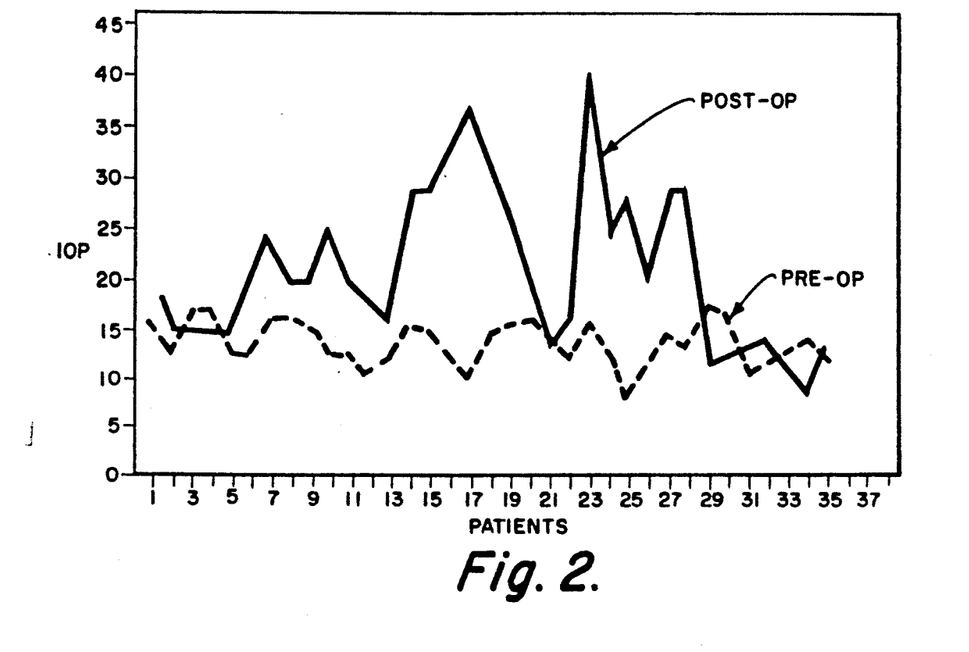
FIG. 2 is a set of curves showing pre-operative and post-operative intraocular pressure IOP in a group of patients receiving Miochol with Diamox.
Figure 3:
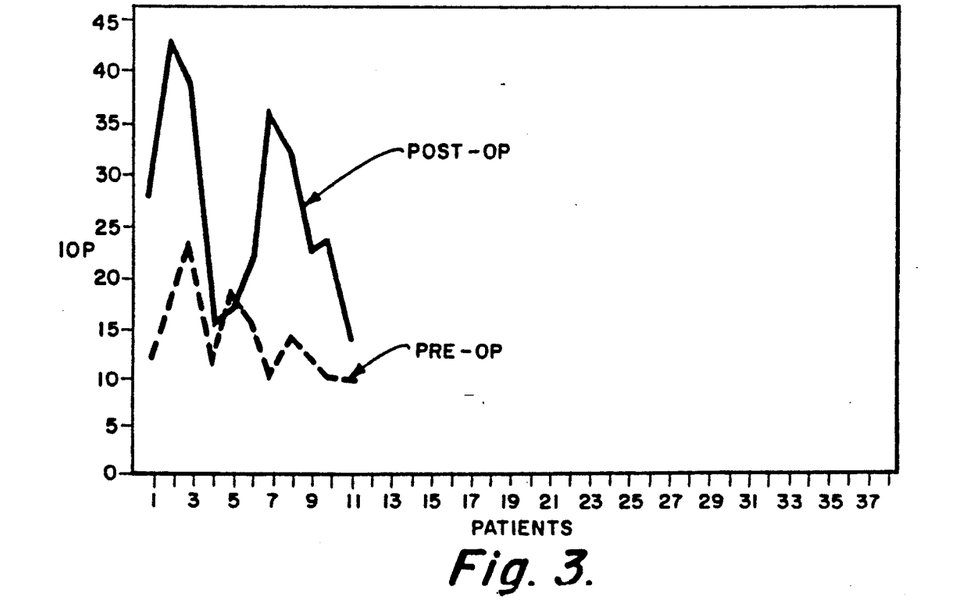
FIG. 3 is a set of curves showing pre-operative and post-operative intraocular pressure IOP in a group of patients receiving Miochol without Diamox.
Figure 4:
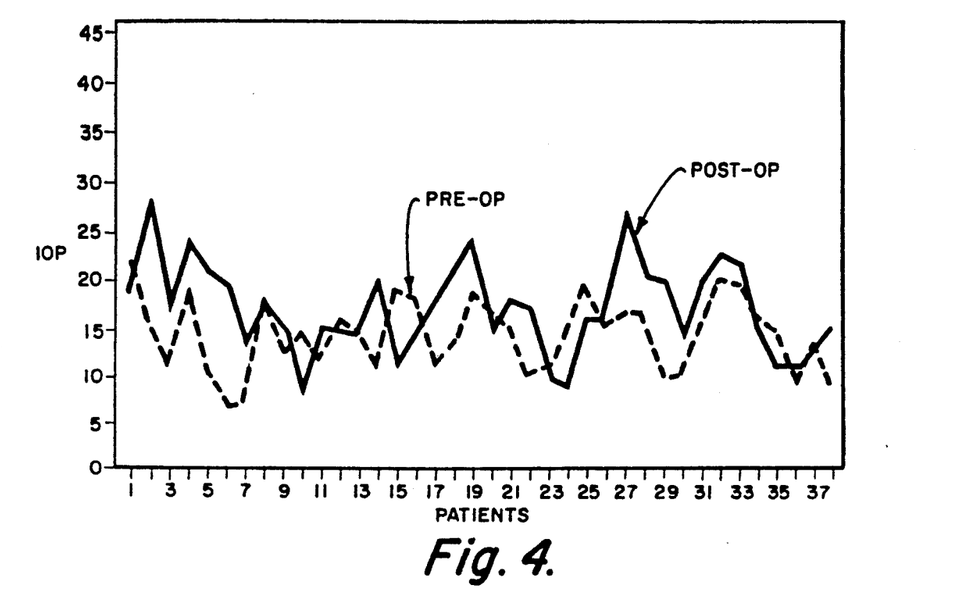
FIG. 4 is a set of curves showing pre-operative and post-operative intraocular pressure IOP in a group of patients receiving Miostat with Diamox.
Figure 5:
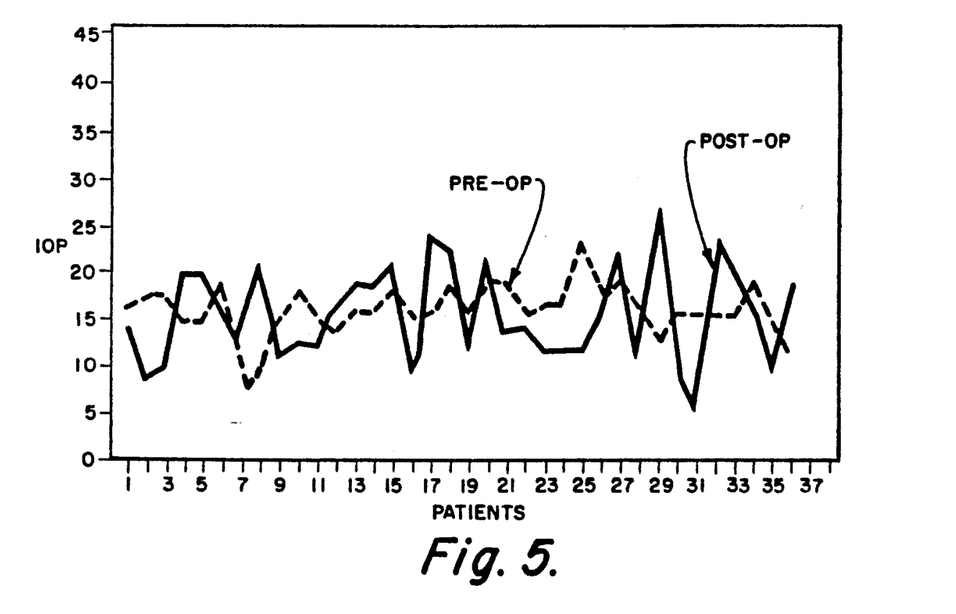
FIG. 5 is a set of curves showing pre-operative and post-operative intraocular pressure IOP in a group of patients receiving Miostat without Diamox.

In the early stages of this retrospective study, it became apparent that post-operative pressure spikes occurring 20–24 hours later were of a major concern. This retrospective study compares the post-operative intraocular pressure (IOP) in 4 groups following standard extracapsular cataract extraction with intraocular lens (ECCE with IOL). The 4 groups consisted of Miochol (acetylcholine chloride) alone, Miochol with 500 mg. Diamox (acetazolamide) given orally at 1800 hours, Miostat (Carbachol) with 500 mg. Diamox given orally at 1800 hours, and fourthly, Miostat alone. FIGS. 2 and 3 show the spiking behavior of the group of patients treated with Miochol with or without Diamox. FIGS. 4 and 5 show that the patients treated with Miostat with or without Diamox had good control of IOP. Surprisingly, the group not receiving Diamox had better control.

The patients given Miochol only had an average pre-operative intraocular pressure of 14.2 and an average post-operative pressure of 26.5. However, 4 of these 11 patients had pressure spikes of over 30, and 1 of 44 mm Hg. The average increase in intraocular pressure was 12.3 mm Hg.

35 patients were given Miochol at the time of surgery with 500 mg. of Diamox orally at 1800 hours on the day of surgery, in an attempt to reduce pressure spikes. The average post-operative pressure was 20.1 with an average increase of 6.8 mm Hg. of pressure. However, in this group, there were 9 of 35 patients with intraocular pressure of above 25 to as high as 42.

38 patients were given Miostat at the time of surgery with Diamox 500 mg. at 1800 hours the day of surgery. The average post-operative intraocular pressure was 16.9, and the average increase in intraocular pressure was 2.3 mm. Only 3 of 38 patients had pressures over 25, the highest being 29. This appeared to be an improvement in control of intraocular pressure 20–24 hours later over both groups of patients using Miochol.

36 patients received only Miostat at surgery with no Diamox given the day of surgery. The average post-operative intraocular pressure was reduced 0.8 mm. Only 1 of 36 patients had a post-operative intraocular pressure of over 25. This group appeared to be clinically at least as well controlled as the Miostat with Diamox group, and certainly superiorly controlled to the Miochol group.

During this retrospective study, 16 known cases of glaucoma were uncovered--an admittedly small group. All glaucoma cases were on medication and felt to be controlled, although 2 patients, 1 in each group, did have a pre-operative pressure of 25. 8 of these patients had been given Miochol at surgery, and 8 had been given Miostat. All of these patients received Diamox 500 mg. at 1800 hours the day of surgery. (a) The surgical technique was the same except a full iridectomy was performed when indicated. (b) Injectable medications at the time of surgery were Garamycin and Celestone. (c) Topical medication used upon completion at surgery were Tobrex, Maxidex, and Betoptic. 500 mg. of Diamox was used orally at 1800 hours the day of surgery in all cases.

Figure 6:
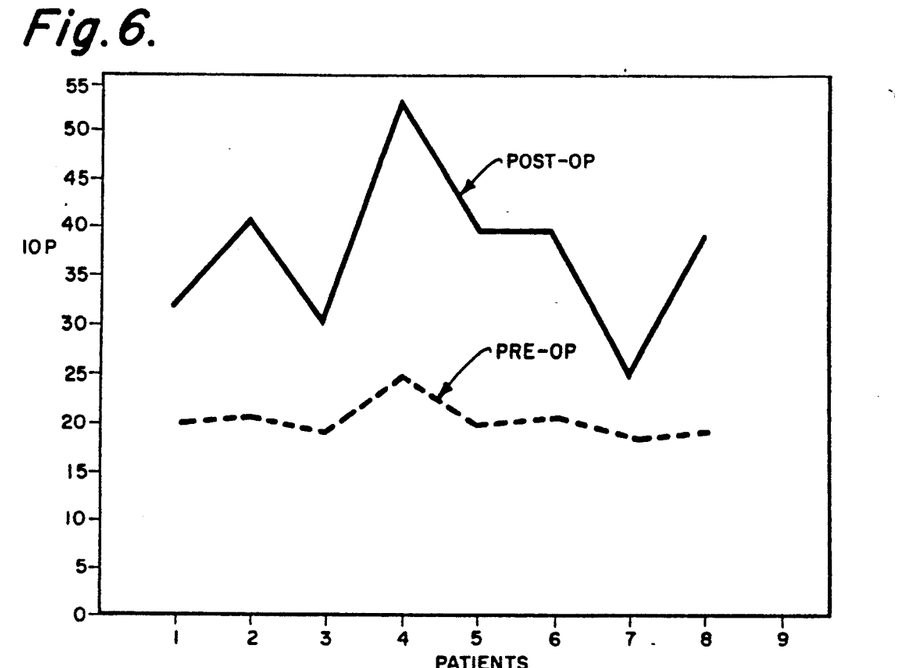
FIG. 6 is a set of curves showing pre-operative and post-operative intraocular pressure IOP in a group of glaucoma patients receiving Miochol.

FIG. 6 shows the data for the 8 patients who had been given Miochol at surgery. The average pre-operative intraocular pressure was 21, and the average post-operative intraocular pressure was 37, an increase of 16.3 mm. 7 of the 8 patients had intraocular pressures of 30 or over, one patient's pressure spiked to 54 mm.

Figure 7:
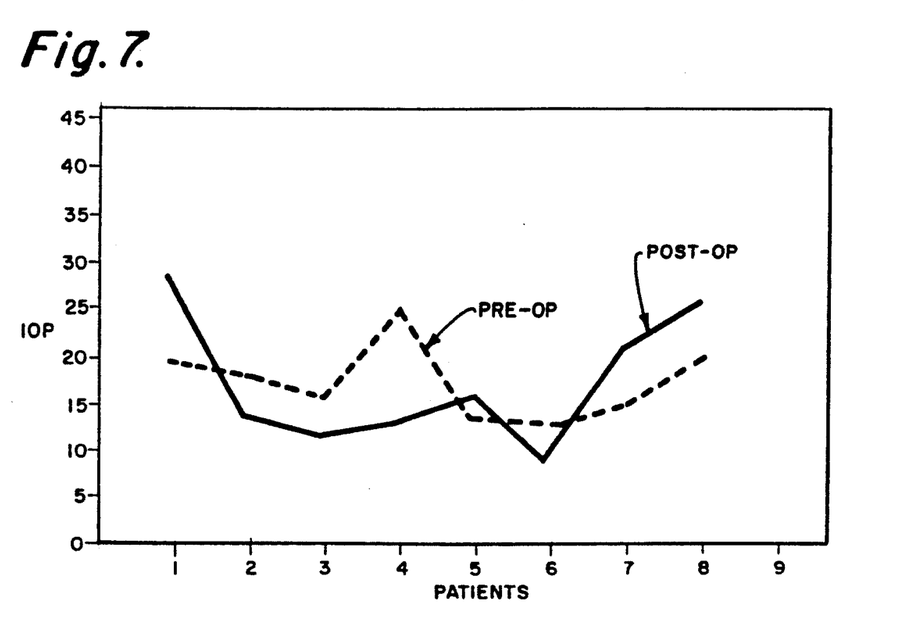
FIG. 7 is a set of curves showing pre-operative and post-operative intraocular pressure IOP in a group of glaucoma patients receiving Miostat.

FIG. 7 shows the data for the 8 patients who had been given Miostat at surgery. Average pre-operative intraocular pressure was 17, and the average post-operative intraocular pressure was the same. Only 2 patients had intraocular pressures above 21, one patient of 26 and one patient of 28. A comparison of the post-operative intraocular pressures in the glaucoma population indicates that there was significant spiking of intraocular pressure 20-24 hours later in the Miochol group compared to the Miostat group of patients.

This retrospective, clinical study of the use of standard ECCE supports the safety and efficacy of the combined miotic agent of the invention. The miotic agent containing both Miochol and Miostat (carbachol 0.01%) appears to be a superior pharmacological agent to one containing Miochol (acetylcholine chloride 1%) in controlling IOP 20-24 hours later, as measured by applanation tonometry. In the routine care of standard ECCE with IOL, Diamox 500 mg. orally at 1800 hours does not seem necessary, if using the miotic agent of the invention containing both Miochol and Miostat. In glaucoma cases, the miotic agent of the invention should be effective in providing quick miosis while controlling post-operative IOP 20-24 hours later.

It is to be realized that only preferred embodiments of the invention have been described and that numerous substitutions, modifications and alterations are permissible without departing from the spirit and scope of the invention as defined in the following claims.

I claim:

1. A method of inducing quick miosis while controlling intraocular pressure in a mammal during ocular surgery comprising the steps of:
    topically applying a viscoelastic agent to the eye of the mammal during surgery;
    topically applying to the eye of the mammal during said surgery a composition containing from 0.1 to 5% by weight of a first miotic agent in a pharmacologically acceptable aqueous carrier, said first agent being selected from compounds of the formula:

where R and $R^1$ are lower alkyl groups containing 1 to 5 carbon atoms and $X^-$ is an anion; and
    topically applying to the eye of the mammal during said surgery a composition containing 0.001 to 1.0 percent by weight of a second miotic agent dissolved in pharmacologically acceptable carrier selected from compounds of the formula:

where $R^2$ is a lower alkyl group of 1-5 carbon atoms, n is an integer from 0-3 and $X^-$ is an anion.

2. A method according to claim 1 in which R and R' are methyl, $R^2$ is methyl, n is O and $X^-$ is chloro.

3. A method according to claim 2 in which the two agents are applied to the eye sequentially.

4. A method according to claim 3 in which the first agent is applied to the eye before the second agent.

5. A method according to claim 2 in which the two agents are applied to the eye simultaneously.

6. A method according to claim 1 in which both miotic agents are dissolved in a pharmacologically acceptable aqueous saline as a common carrier.

7. A method according to claim 1 in which the mammal is a human.

8. A Method according to claim 7 in which the human subject is undergoing extracapsular cataract extraction with intraocular lens implant surgery.

9. A method according to claim 8 in which the human subject is suffering from glaucoma.

10. A method according to claim 1 in which said both carries are aqueous carriers.

11. A unit dosage package containing a combination of a miotic agent capable of achieving quick miosis and an agent for controlling intraocular pressure, comprising:
    a first sterile compartment containing a unit dosage of a solution comprising 0.001 to 1.0 percent by weight of a first compound of the formula:

where $R^2$ is a lower alkyl group of 1-5 carbon atoms, n is an integer from 0-3 and $X^-$ is an anion;
    a second sterile compartment containing a unit dosage in dry powder form of a second compound selected from compounds of the formula:

where R and $R^1$ are lower alkyl groups containing 1-5 carbon atoms and $X^-$ is an anion;
    said second compound having a concentration of 0.1 to 5 percent by weight when dissolved in said solution; and
    means for combining the contents of the first and second compartments.

12. A package according to claim 11 in which the containers are physically joined.

13. A package according to claim 12 in which the containers are joined by an elastomer seal penetrable by a hypodermic needle.

14. A package according to claim 11 in which R and $R^1$ are methyl, $X^-$ is chloro and $R^2$ is methyl, n is O and $X^-$ is chloro.

15. A unit dosage package according to claim 11 in which the package is a univial containing an elastomer plug dividing the univial into said first and second compartments.

16. A topical, ophthalmic, pharmaceutical composition for achieving quick miosis and for controlling intraocular pressure, comprising:
    0.1 to 5 percent by weight of a first compound selected from compounds of the formula:

where R and $R^1$ are lower alkyl groups containing 1 to 5 carbon atoms and $X^-$ is an anion; and
    0.001 to 1.0 percent by weight of a second compound selected from the formula:

where $R^2$ is a lower alkyl group of 1–5 carbon atoms, n is an integer from 0–3 and $X^-$ is an anion; and a pharmacologically acceptable carrier.

17. A composition according to claim 16 in which the carrier is an aqueous carrier.

18. A composition according to claim 16 in which the first compound is acetylcholine and the second compound is carbachol.

* * * * *